US00PP19059P2

(12) United States Plant Patent
Chaney

(10) Patent No.: US PP19,059 P2
(45) Date of Patent: Jul. 29, 2008

(54) ***PHORMIUM* PLANT NAMED 'JUBILEE'**

(50) Latin Name: *Phormium tenax*
Varietal Denomination: Jubilee

(76) Inventor: Christopher Chaney, 2425 Mesa Ranch Rd., Arroyo Grande, CA (US) 93420

( * ) Notice: Subject to any disclaimer, the term of this patent is extended or adjusted under 35 U.S.C. 154(b) by 0 days.

(21) Appl. No.: 11/804,762

(22) Filed: May 21, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para

(57) ABSTRACT

A new cultivar of *Phormium* plant named 'JUBILEE' which exhibits an upright clumping habit and appears to be bright red by virtue of the prominent red margins of the upper leaf surface and the redness of the entire lower leaf surface. In combination these traits set 'JUBILEE' apart from all other existing varieties of *Phormium* known to the inventor.

3 Drawing Sheets

Genus: *PHORMIUM.*
Species: *tenax.*
Denomination: 'JUBILEE'.

BACKGROUND OF THE INVENTION

The present invention relates to a new and distinct variety of New Zealand flax grown for use in the landscape, or for use as a container plant. The new cultivar is known botanically as *Phormium tenax* and will be referred to hereinafter by the cultivar name 'JUBILEE'.

'JUBILEE' is a naturally occurring and plant mutation that was discovered by the inventor at the inventor's nursery in Arroyo Grande, Calif. 'JUBILEE' arose as follows:

In 2000, the inventor purchased a *Phormium* plant labeled as *Phormium* 'Red Heart' (unpatented) from a commercial nursery in California. The inventor was attracted to 'Red Heart' by its foliage which was predominantly red on its upper surface with narrow green margins.

*Phormiums* may be propagated by division of the basal clump, and the divided elements may be described as fans. In 2000, the inventor decided to propagate the purchased plant and by 2003 had built up a stock of approximately 2,000 plants in one gallon containers. Meanwhile, the inventor made enquiries with other California nurseries that produce and known *Phormiums.* The inventor has concluded that 'Red Heart' was a local misnomer, and that the purchased plant was a plant of the *Phormium* variety named 'Jester' (unpatented) which had entered commerce around the time of the inventor's original purchase.

In 2003, the inventor observed that one section of the basal clump of one plant of 'Jester' appeared to carry the reverse variegation compared to its parent. Instead of bearing predominantly red foliage with a green margin (upper leaf surface), the observed section exhibited predominantly green foliage with a red margin. The inventor considers that this atypical growth arose as a spontaneously occurring mutation.

In 2003, the inventor excised this one section to make a single fan for establishing as a new plant growing on its own roots in Arroyo Grande, Calif. The fan grew successfully and the inventor has subsequently propagated repeatedly from the original, using the method of division. The inventor has determined that all plants subsequently propagated have remained true to the type of the original observed mutation.

The inventor has named this new cultivar 'JUBILEE', the subject of the present specification.

In comparison with the parent variety, 'Jester', which is also the variety of *Phormium* which the inventor considers most closely resembles 'JUBILEE', 'JUBILEE' exhibits the following distinguishing characteristics: First, the variegation of the upper surface of the leaves is reversed as between 'Jester' and 'JUBILEE', as described herein. Second, whereas the lower leaf surface of 'Jester' is green, the color of the lower leaf surface of 'JUBILEE' is red with dark stripes. Third, when comparing plants of similar age, the width of the leaves of 'JUBILEE' is approximately half of the width of the leaves of 'Jester'. Fourth, 'JUBILEE' appears to be faster growing that 'Jester', with a denser and more tightly clumping habit achieved in the same growing period.

'JUBILEE' is a vigorous plant with an upright clumping habit. To the observer, 'JUBILEE' appears to be bright red by virtue of the prominent red margins of the upper leaf surface and the redness of the entire lower leaf surface.

Cultural requirements include full sun to part shade, occasional to regular water, and well-draining loam soil.

There is not resistance or susceptibility to any pests or disease known to the inventor.

'JUBILEE' has produced no flowers to date.

SUMMARY OF THE INVENTION

The following traits have been repeatedly observed and represent the distinguishing characteristics of the new *Phormium* variety named 'JUBILEE'. In combination these traits set 'JUBILEE' apart from all other *Phormium* known to the inventor. 'JUBILEE' has not been tested under all possible conditions and phenotypic differences may be observed with variations in environmental, climatic and cultural conditions, however, without any variance in genotype.

1. 'JUBILEE' exhibits upright clumping habit and is vigorous.
2. 'JUBILEE' is fan-shaped with long narrow leaves which arch when fully extended.
3. The upper leaf surfaces of 'JUBILEE' are green with bright red margins which extend inwards to occupy approximately one half of the leaf width.

4. The lower leaf surfaces of 'JUBILEE' are predominantly red with dark stripes.
5. Cultural requirements for 'JUBILEE' are full sun to partial shade, occasional to regular water, and well-draining soil.
6. 'JUBILEE' has produced no flowers to date.
7. 'JUBILEE' is hardy to USDA Zone 8.

BRIEF DESCRIPTION OF THE DRAWINGS

The accompanying color drawings illustrate the overall appearance of the new *Phormium* cultivar named 'JUBILEE' showing the colors as true as it is reasonably possible to obtain in colored reproductions of this type. Colors in the drawings may differ from the color values cited in the detailed botanical description, which accurately describes the actual colors of the new variety 'JUBILEE'. Drawings were made in Santa Barbara, Calif. in January 2007 from a two year old plant which had been grown in a 3 gallon container plant outdoors in coastal California in full sun.

The drawing labeled as FIG. 1 depicts a side view of the plant illustrating foliage and plant habit.

Figure 1:
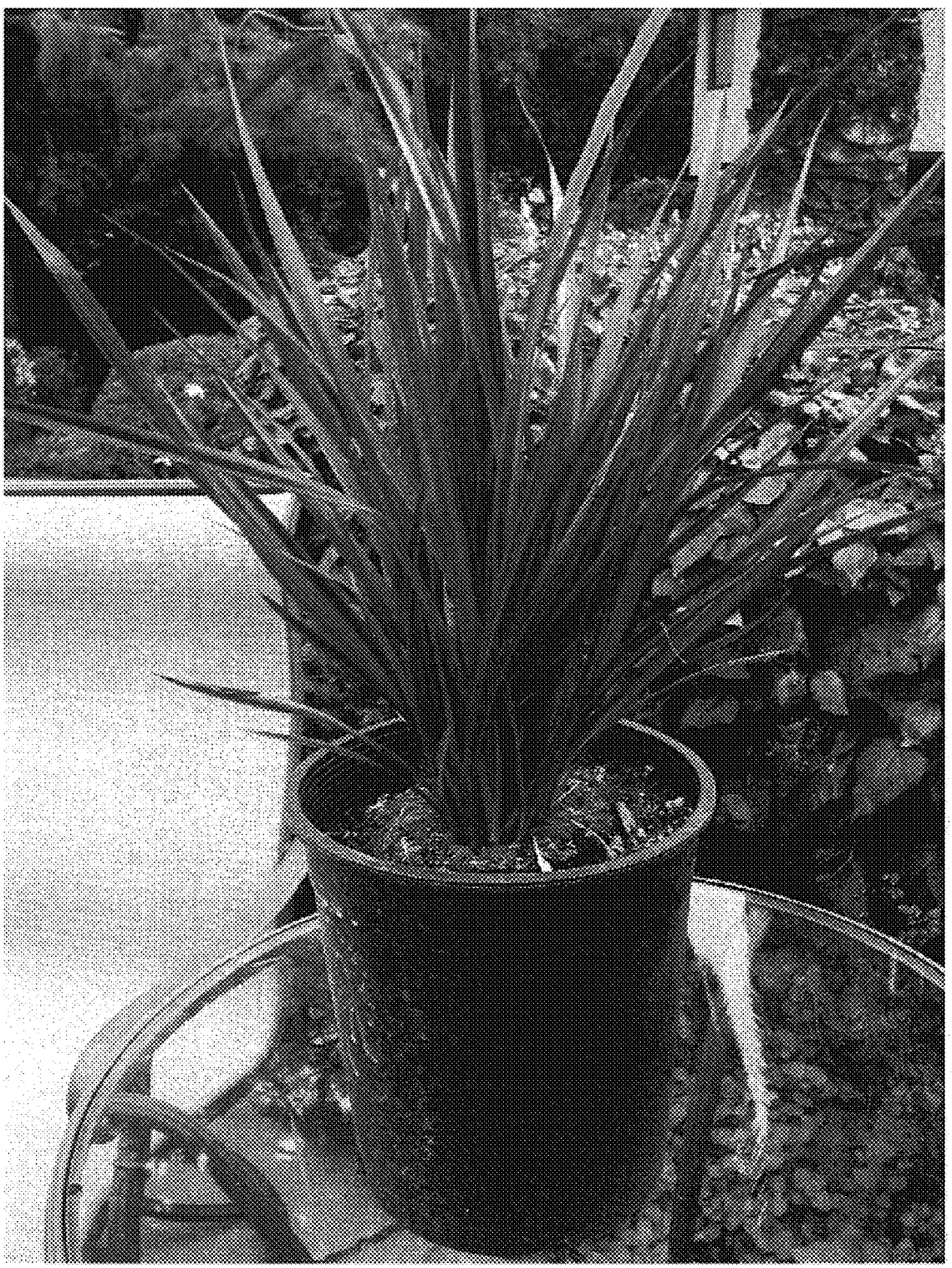
Figure 2:
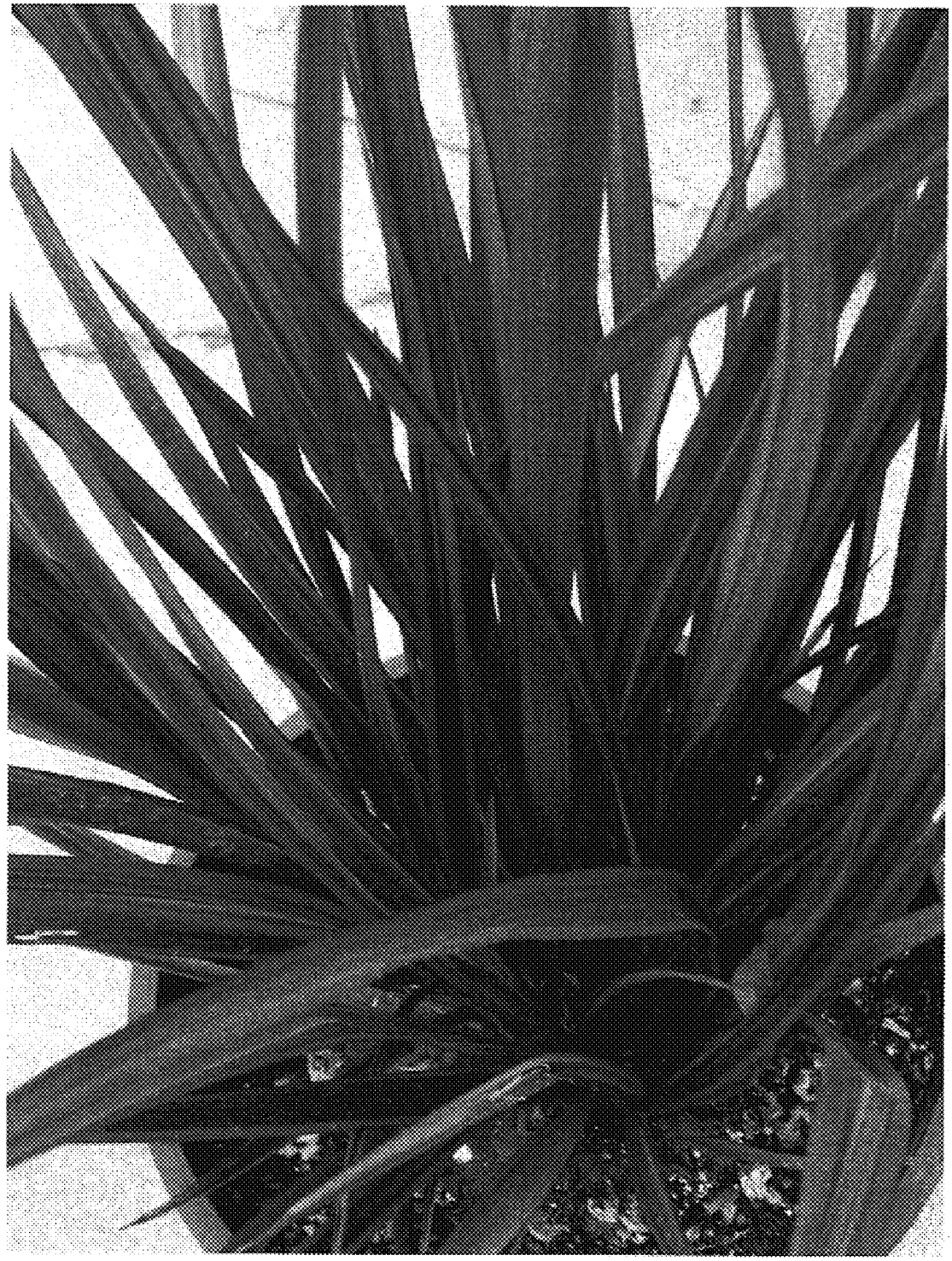

The drawings labeled as FIG. 2 depicts a close up view of the foliage and leaf margins of 'JUBILEE'.

Figure 3:
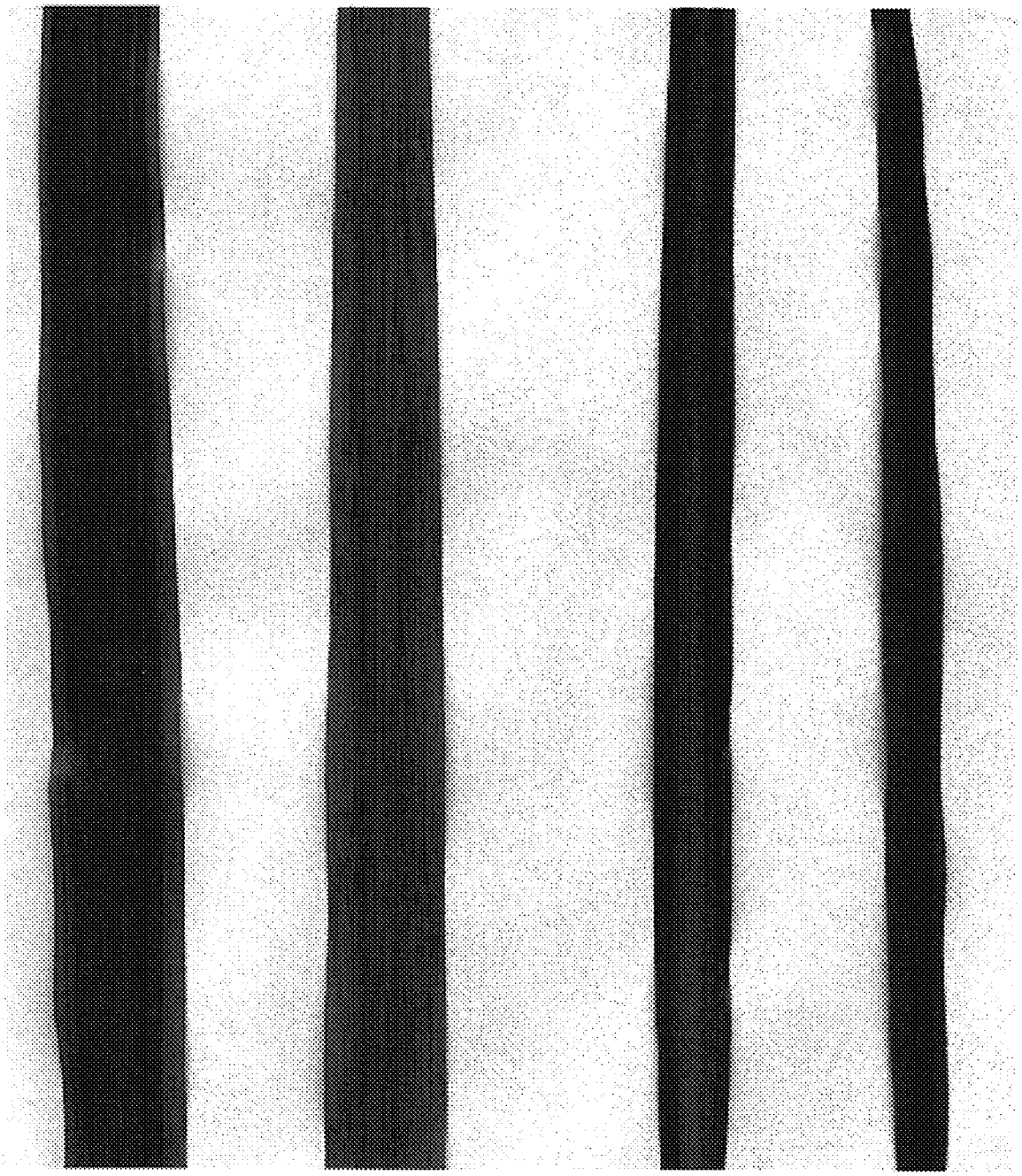

The drawing labeled FIG. 3 compares the widths and the colors of the foliage of 'JUBILEE' with the width and colors of the foliage of the parent plant 'Jester'. The plants from which these drawings were made were of similar age, approximately two years old. The arrangement of the views is as follows, from left to right:

First (extreme left), the adaxial surface of the wider-leaved 'Jester',

Second, the abaxial surface of 'Jester',

Third, the adaxial surface of the narrower leaves 'JUBILEE',

Fourth (extreme right), the abaxial surface of 'JUBILEE'.

The drawings were made using conventional techniques and although colors may appear different from actual colors due to light reflectance they are as accurate as possible by conventional photography.

DETAILED BOTANICAL DESCRIPTION

The following is a detailed description of the new *Phormium* plant named 'JUBILEE'. Data was collected in Santa Barbara, Calif. from a 2 year old plant growing in full sun out-of-doors in a 3 gallon container. The color determinations are in accordance with the 2001 edition of The Royal Horticultural Society Colour Chart, of London, England, except where general color terms of ordinary dictionary significance are used.

Botanical classification: *Phormium tenax* 'JUBILEE'.
Genus: *PHORMIUM.*
species: *tenax.*
Denomination: 'JUBILEE'.
Common name: New Zealand flax.
Plant type: Perennial.
Commercial classification: Evergreen shrub.
Commercial container size: 3 gallon.
Plant use: Recommended for use in the landscape, or for use as a container plant.
Cultural requirements: Cultural requirements are full sun to partial shade, occasional to regular water, and well-draining loam soil.
Parentage: *Phormium tenax* 'JUBILEE' was discovered as a naturally occurring mutation from an individual plant of *Phormium tenax,* 'Jester' (unpatented) within a commercial crop of *Phormium tenax* 'Jester'.
Disease and pests susceptibility or resistance: There is no disease or pest resistance or susceptibility known to the inventor.
Plant description:
*Bloom period.*—No flowers have been produced to date.
*Plant habit.*—Upright clumping.
*Plant size.*—Small to medium size relative to the genus *Phormium* as a whole.
*Root system.*—Fibrous and fleshy.
*Plant vigor.*—Vigorous; produces many slender leaves.
*Plant shape.*—Fan-shaped, foliage slightly arching when fully extended.
*Plant height.*—70 cm.—75 cm.
*Plant width.*—45 cm.—60 cm.
*Plant hardiness.*—USDA Zone 8.
*Plant propagation.*—Tissue culture and division.
*Time to develop roots.*—From a tissue culture explant, in greenhouse conditions and a rooting temperature in range 20° C.–25° C.: 2 months. As a plant division rooting in ambient temperatures outdoors in coastal California (typically 10° C.–15° C. at night, 18° C.–25° C. in day): 3–4 weeks.
*Crops time* (*3 gallon container*).—From 18 to 24 months from a weaned tissue culture microplant or from a plant division.
Foliage:
*Branching pattern.*—Dense basal rosette.
*Foliage type.*—Evergreen.
*Quantity of leaves.*—Approximately 60.
*Leaf arrangement.*—Equitant, folded lengthwise and keeled on dorsal surface.
*Leaf shape.*—Gladiate.
*Leaf division.*—Simple.
*Leaf attachment.*—Sessile, basally sheathing.
*Leaf apex.*—Broadly acute.
*Leaf base.*—Truncate.
*Leaf margin.*—Entire.
*Leaf blade surface* (*both surfaces*).—Minutely furrowed.
*Leaf pubescence* (*both surface*).—None.
*Leaf width* (*oldest leaves*).—1.5 cm.
*Leaf length* (*oldest leaves*).—70 cm–75 cm.
*Leaf fragrance.*—No fragrance observed.
*Leaf colors* (*adaxial surface*).—Margination (each margin represents approximately 25% of leaf total width): Ranges from 47A to 53B. Leaf center (represents approximately 50% of total leaf width): 147A. Veins parallel, either inconspicuous, color as adjacent leaf surface, or appearing as stripes, width 1 mm–3 mm, color N189A.
*Leaf colors* (*abaxial surface*).—No margination. Leaf: Ranges from 47A to 53B. Veins parallel, either inconspicuous, color as adjacent leaf surface, or appearing as stripes, width 1 mm–4 mm, color N189A.
Flower:
*JUBILEE* has produced no flowers to date.

What is claimed is:

1. A new and distinct cultivar of *Phormium* plant named 'JUBILEE' as described and illustrated herein.

* * * * *